(12) United States Patent
Chambaud et al.

(10) Patent No.: US 8,557,561 B2
(45) Date of Patent: Oct. 15, 2013

(54) **STRAIN OF *LACTOBACILLUS PARACASEI* HAVING ANTIMICROBIAL AND IMMUNOMODULATORY PROPERTIES**

(75) Inventors: Isabelle Chambaud, Issy les Moulineaux (FR); Artem Khlebnikov, Boulogne (FR); Anne-Catherine Villain, Juvisy sur Orge (FR); Gianfranco Grompone, Paris (FR); Thierry Saint Denis, Vincennes (FR); Anne Druesne, Bures sur Yvette (FR); Tamara Smokvina, Orsay (FR)

(73) Assignee: Compagnie Gervais Danone, Paris (FR)

( * ) Notice: Subject to any disclaimer, the term of this patent is extended or adjusted under 35 U.S.C. 154(b) by 307 days.

(21) Appl. No.: 12/988,431

(22) PCT Filed: Apr. 16, 2009

(86) PCT No.: PCT/FR2009/000443
§ 371 (c)(1),
(2), (4) Date: Dec. 10, 2010

(87) PCT Pub. No.: WO2009/130423
PCT Pub. Date: Oct. 29, 2009

(65) Prior Publication Data
US 2011/0150852 A1    Jun. 23, 2011

(30) Foreign Application Priority Data
Apr. 18, 2008 (FR) .................... 08 02158

(51) Int. Cl.
*C12N 1/20* (2006.01)

(52) U.S. Cl.
USPC ...................... 435/252.9; 424/93.45

(58) Field of Classification Search
None
See application file for complete search history.

(56) References Cited

U.S. PATENT DOCUMENTS

2004/0110270 A1 * 6/2004 Dennin et al. ............. 435/252.5

FOREIGN PATENT DOCUMENTS

| WO | WO 96/20607 | 7/1996 |
| WO | WO 02/053706 | 7/2002 |
| WO | WO 2007043933 A1 * | 4/2007 |
| WO | WO 2008/047391 | 4/2008 |

OTHER PUBLICATIONS

Ljungh, Isolation, Selection and Characteristics of *Lactobacillus paracasei* Subsp. *paracasei* F19, Microbial Ecology in Health and Disease, 14, 4-6, 2002.

* cited by examiner

*Primary Examiner* — Allison Ford
*Assistant Examiner* — Susan E Frenandez
(74) *Attorney, Agent, or Firm* — Morgan, Lewis & Bockius LLP

(57) ABSTRACT

The invention relates to a novel strain of *Lactobacillus paracasei* subspecies *paracasei*, having antimicrobial and immunomodulatory properties, and to compositions containing said strain.

3 Claims, 3 Drawing Sheets

SEQUENCE LISTING

<160> NUMBER OF SEQ ID NOS: 4

<210> SEQ ID NO 1
<211> LENGTH: 3323
<212> TYPE: DNA
<213> ORGANISM: Lactobacillus paracasei

<400> SEQUENCE: 1

```
gttttccccg cacatgcggg ggtgatcctt acaagctgaa tggtacgcca cagccagcgc      60
tgttttcccc gcacatgcgg gggtgatccc tacatcaacg aaacgctgat aacgcgatca     120
gcgttttccc cgcacatgcg ggggtgatcc tgagatcagg gtttatccaa ctaccgtctt     180
caagttttcc ccgcacatgc gggggtgatc cctgatctca aagccttatc cagcatcaga     240
tattgttttc cccgcacatg cggggggtgat cctggatcag gcaaaaggcg atcttgataa     300
ctacagtttt ccccgcacat gcggggggtga tccctgttta gcctaatcat taagcgcctc     360
aacgttgttt tccccgcaca tgcggggggtg atccctgtat gaacccatta cgcttgccat     420
gcttgctgtt ttccccgcac atgcgggggt gatcctatca agcccgatta tttggttcac     480
gattctaagt tttccccgca catgcggggg tgatccttat gtcattagga acgaatgcct     540
atcaacatag ttttccccgc acatgcgggg gtgatcctaa ccgtttagaa gggatcacta     600
gccagctgaa gttttccccg cacatgcggg ggtgatcctg taaatgtccg cgtccgatgg     660
ttcgtccgcc ggttttcccc gcacatgcgg gggtgatcct ggtaaattgc aggctcaata     720
tacccagcta aagttttccc cgcacatgcg ggggtgatcc cgcccctcc cgcataacct     780 gtgttgtcta aacgttttcc ccgcacatgc gggggtgatc caaaccaaga gcaacaaat     840 gttattaagc cattgttttc cccgcacatg cgggggtgat cctacgctca atctgcagct     900
tgctggtatt gttcagtttt ccccgcacat gcgggggtga tcccttggtt atcaagcgac     960
acagacccca caaacagttt tccccgcaca tgcggggggtg atcccagaat aatgttctta    1020
aagctgtcct tggtgaggtt ttcccgcac atgcgggggt gatcccgcgg ccgtaacagc    1080
ggcagaacag cttggtgtgt tttccccgca catgcggggg tgatcctaag gtgagtgcat    1140
atgtctaaaa aaattgatcg ttttccccgc acatgcgggg gtgatcctat ggcagctaat    1200
```

```
acggatgcca ttttagctgg gttttccccg cacatgcggg ggtgatcccg gactgctagt    1260
agtatcaaaa tacatgatga ggttttcccc gcacatgcgg gggtgatccc gacaagttcg    1320
gaatttctca gattggcggt tagttttccc cgcacatgcg ggggtgatcc ccaagataaa    1380
tctatatctt tgcaataaat agcgttttcc ccgcacatgc ggggtgatc ccggtggtat    1440
cccaaacttt tgacataccc tttggttttc cccgcacatg cggggtgat cctaaatgtt    1500
cccttaatcc tcaaaaggcc tttcggtttt ccccgcacat gcgggggtga tccccaatga    1560
cattattttt ataatcagtc atttctgttt tccccgcaca tgcgggggtg atcccaaaat    1620
gccgaaggtc aacaaaaatg gtgatccgtt ttccccgcac atgcggggt gatcccaatg    1680
catcaaacac catttcgaag ggcattaggt tttccccgca catgcgggg tgatcccaac    1740
agatgatgtc aaaatcccag caagtgattg ttttccccgc acatgcgggg gtgatccccg    1800
ctgaaatatc gctaatcatg ccatcaatga gttttccccg cacatgcggg ggtgatcccc    1860
attcaggaga tctcgaatac gcttttcttt agttttcccc gcacatgcgg gggtgatccc    1920
cagccactgg taaacctgat cggtgttgat tagttttccc cgcacatgcg ggggtgatcc    1980
tggtcattga tgattaaaaa caagccaatg gcagttttcc ccgcacatgc ggggtgatc    2040
ctaactggct caacaggata agtgccacca ttatgttttc cccgcacatg cggggggtgat    2100
cccatcgtct tctgtataag aagacggatc agatggtttt ccccgcacat gcggggtga    2160
tccttacttg tccgactaat ggactgactg agaatggttt tccccgcaca tgcggggtg    2220
atcctaaagc tggttacaag gtaccggcca acatgggggtt ttccccgcac atgcggggt    2280
gatcctacca taggttggct gggtttaacg caatgtgagt tttccccgca catgcggggg    2340
tgatcccaac aatttacaaa acgccattca agaaagttag ttttccccgc acatgcgggg    2400
gtgatcctca gacttagccg aatccacctt cttgtctttg gttttccccg cacatgcggg    2460
ggtgatcccc agtcagagta atgtgggggc cagacgaaat agttttcccc gcacatgcgg    2520
gggtgatccc gagatcattc aacacatata ttcacctcca cagttttccc cgcacatgcg    2580
ggggtgatcc tactagtcca tatcagctgg agatcagcgc ctagttttcc ccgcacatgc    2640
gggggtgatc ccacctaaag atgtggaagc atgaccatgg agacgttttc cccgcacatg    2700
cggggggtgat cctggcaagt gacgctaaag gatcacacca atactgtttt ccccgcacat    2760
gcgggggtga tcccagtagt tactatgcgt caaacaagca gattttgttt tccccgcaca    2820
tgcggggggtg atccctacaa agacaagtac gcgtttgctc gcaagatgtt ttccccgcac    2880
atgcggggggt gatcctacta agggagacgg cggtaagtat ggacatttgg ttttcccccgc    2940
acatgcgggg gtgatcctaa caacattaaa ggtgaatgcc gccactgcaa gttttccccg    3000
cacatgcggg ggtgatcctg gtcaagctcg gcaagatttc gccagcgtgg ggttttcccc    3060
gcacatgcgg gggtgatccc aatcggtgca cgtccggctg ttggtaagtc gggttttccc    3120
cgcacatgcg ggggtgatcc ttgtcgccat tctttgacgg agtttgaccc tgagttttcc    3180
gcgcacatgc ggggtgatc ccatggctag cgatggtatt atttctgggg ctgagttttc    3240
cgcgcacatg cggggggtgat cctatcagcc ggaagcggtg aagctggcgc gtttggtttt    3300
ccccgcacat gcggggggtga tcc                                            3323
```

<210> SEQ ID NO 2
<211> LENGTH: 28
<212> TYPE: DNA
<213> ORGANISM: Lactobacillus paracasei

<400> SEQUENCE: 2

```
gttttccccg cacatgcggg ggtgatcc                                              28

<210> SEQ ID NO 3
<211> LENGTH: 20
<212> TYPE: DNA
<213> ORGANISM: Lactobacillus paracasei

<400> SEQUENCE: 3
ctcaacagga taagtgccac                                                       20

<210> SEQ ID NO 4
<211> LENGTH: 19
<212> TYPE: DNA
<213> ORGANISM: Lactobacillus paracasei

<400> SEQUENCE: 4
ggttggctgg gtttaacgc                                                        19
```

STRAIN OF *LACTOBACILLUS PARACASEI* HAVING ANTIMICROBIAL AND IMMUNOMODULATORY PROPERTIES

RELATED APPLICATIONS

The present application is a U.S. National Phase Application of International Application No. PCT/FR2009/000443 (filed Apr. 16, 2009) which claims priority to French Patent Application No. 0802158 (filed Apr. 18, 2008) which are hereby incorporated by reference in their entirety.

SEQUENCE LISTING SUBMISSION VIA EFS-WEB

A computer readable text file, entitled "045636-5151_SequenceListing.txt," created on or about Oct. 18, 2010 with a file size of about 6 kb contains the sequence listing for this application and is hereby incorporated by reference in its entirety.

The invention relates to a novel strain of *Lactobacillus paracasei* subsp. *paracasei* having antimicrobial and immunomodulatory properties.

A very large number of scientific studies have reported the beneficial effects, on the health, of certain microorganisms present in fermented foodstuffs, in particular dairy products. These microorganisms are commonly referred to as "probiotics". According to the definition generally accepted at the current time, probiotics are: "live microorganisms which, when they are consumed in appropriate amounts, have a beneficial effect on the health of the host" (FAO/WHO report on evaluation of health and nutritional properties of probiotics in food, including powder milk containing live lactic acid bacteria; Cordoba, Argentina; Oct. 1-4, 2001).

It has been shown that the consumption of food products containing probiotic bacteria can produce favorable effects on the health, in particular through re-equilibrating the intestinal flora, improving resistance to infections, and modulating the immune response.

The probiotic microorganisms used in human food are generally lactic acid bacteria belonging mainly to the *Lactobacillus* and *Bifidobacterium* genera, and in particular to the species *Lactobacillus paracasei* subsp. *paracasei* (a strain of which is described in patent application EP0794707).

However, the beneficial effects on the health are not generally common to all the bacteria of the same genus, nor even of the same species. They are, most commonly, encountered only in certain strains; in addition, the effects observed can vary qualitatively and/or quantitatively from one probiotic strain to the other, including within the same species.

In order for it to be possible for a microorganism to be considered potentially usable as a probiotic, it must meet at least one, and ideally several, of the following criteria:

exhibit an inhibitory activity with respect to pathogenic microorganisms that may be present in the intestinal flora, it being possible for this activity to result either from the ability to adhere to the intestinal cells, thus excluding or reducing the adherence of the pathogens, or from the ability to produce substances which inhibit the pathogens, or from the combination of these two characteristics;

exhibit immunomodulatory properties, and in particular immunostimulatory and/or anti-inflammatory properties.

In addition, if this microorganism is intended to be incorporated into a dairy product, it should preferably exhibit satisfactory growth on milk.

Finally, it should maintain good viability, during the production and storage of the foodstuff into which it is incorporated, and also after ingestion of this foodstuff by the consumer, so as to be able to reach the intestine and to survive in the intestinal environment.

It should, however, be noted that, although viability is essential in order to correspond to the current definition of "probiotic", it has been shown that some of the beneficial effects associated with probiotic strains can be obtained even in the absence of live bacteria, and are attributable to certain bacterial fractions or to active fractions of their culture supernatants. For example, PCT application WO2004093898 describes an immunomodulatory preparation obtained by fractionation of the culture supernatant of the CNCM I-2219 strain.

The inventors have now succeeded in isolating a novel strain of *Lactobacillus paracasei* subsp. *paracasei* which meets the criteria indicated above.

A subject of the present invention is this strain, which was deposited, according to the Treaty of Budapest, with the CNCM (Collection Nationale de Cultures de Microorganismes [National collection of microorganism cultures], 25 rue du Docteur Roux, Paris), on Nov. 9, 2006, under number I-3689.

The CNCM I-3689 strain has the following characteristics:

Morphology: Gram-positive microorganism, small thin bacilli, isolated or small chains.

Fermentation of the following sugars (results obtained on an api 50 CH strip-API MRS medium at 37° C. for 48 h): ribose, galactose, D-glucose, D-fructose, D-mannose, mannitol, N-acetylglucosamine, arbutin, cellobiose, maltose, lactose, trehalose, melezitose, D-turanose, D-tagatose, gluconate.

Presence of a single CRISPR locus of sequence SEQ ID NO: 1, containing a repeat sequence represented by the nucleotide sequence SEQ ID NO: 2.

It has, in addition, antimicrobial properties which result in a strong ability to inhibit the growth of pathogenic microorganisms in culture, in particular *Escherichia coli*, *Salmonella enteritidis* and *Listeria monocytogenes*.

The CNCM I-3689 strain also has immunomodulatory, and in particular anti-inflammatory, properties.

The subject of the present invention also encompasses *Lactobacillus paracasei* subsp. *paracasei* strains that can be obtained by mutagenesis or by genetic transformation of the CNCM I-3689 strain. Preferably, these strains retain the antimicrobial and immunomodulatory properties of the CNCM I-3689 strain. They may be strains in which one or more of the endogenous genes of the CNCM I-3689 strain has (have) been mutated, for example so as to modify some of its metabolic properties (e.g. the ability of this strain to metabolize sugars, its resistance to intestinal transit, its resistance to acidity, its post-acidification or its metabolite production). They may also be strains resulting from genetic transformation of the CNCM I-3689 strain with one or more gene(s) of interest, making it possible, for example, to confer additional physiological characteristics on said strain, or to express proteins of therapeutic or vaccine interest, which it is desired to administer by means of said strain.

These strains can be obtained from the CNCM I-3689 strain by means of the conventional techniques for random or site-directed mutagenesis and genetic transformation of lactobacilli, such as those described, for example, by Gury et al. (Arch Microbiol., 182, 337-45, 2004) or by Velez et al. (Appl Environ Microbiol., 73, 3595-3604, 2007), or by the technique known as "genome shuffling" (Patnaik et al. Nat Biotechnol, 20, 707-12, 2002; Wang Y. et al., J. Biotechnol., 129, 510-15, 2007). These strains have in particular a CRISPR locus of sequence SEQ ID NO: 1.

A subject of the present invention is also a method for obtaining a *Lactobacillus paracasei* subsp. *paracasei* strain having antimicrobial and/or immunomodulatory properties, comprising a step of mutagenesis or of genetic transformation of the CNCM I-3689 strain.

A subject of the present invention is also a method for obtaining a cell fraction having antimicrobial and/or immunomodulatory properties, from a *Lactobacillus paracasei* subsp. *paracasei* strain in accordance with the invention. Said cell fractions are in particular DNA preparations or bacterial wall preparations obtained from cultures of said strain. They may also be culture supernatants or fractions of these supernatants.

A subject of the present invention is also compositions comprising a *Lactobacillus paracasei* subsp. *paracasei* strain in accordance with the invention, or a cell fraction obtained from said strain.

These compositions can in particular be lactic ferments, combining a *Lactobacillus paracasei* subsp. *paracasei* strain in accordance with the invention with one or more other, optionally probiotic, strain(s) of lactic acid bacteria. By way of example of strains of lactic acid bacteria, mention may be made of the *Lactobacillus bulgaricus* and *Streptococcus thermophiles* strains.

They may also be food products, and in particular dairy products, or pharmaceutical or cosmetic products comprising a *Lactobacillus paracasei* subsp. *paracasei* strain in accordance with the invention, or a cell fraction obtained from said strain.

When said strain is present in the form of live bacteria, they will preferably be present in a proportion of at least $10^5$ cfu per gram, advantageously at least $10^6$ cfu per gram of product, more advantageously at least $10^7$ cfu per gram, and even more advantageously at least $10^8$ cfu per gram.

The present invention will be understood more clearly from the further description which follows, which refers to examples illustrating the antimicrobial, immunomodulatory and anti-infective properties of the CNCM I-3689 strain, and also the molecular typing of this strain.

EXAMPLE 1

Figure 1:
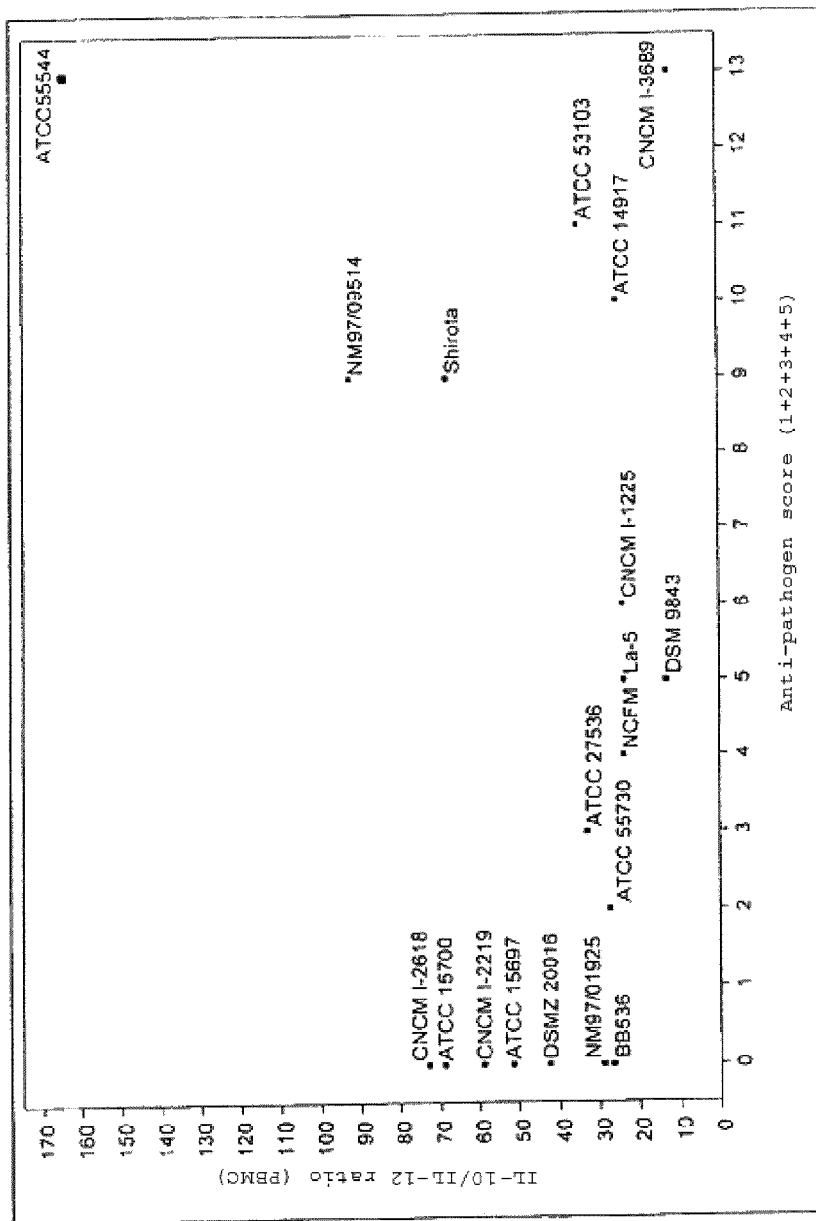
FIG. 1 represents the IL-10/IL-12 ratio of bacterial strains as a function of their anti-pathogen score (arbitrary unit) determined in Table III.

Comparison of the Properties of the CNCM I-3689 Strain with Those of Known Probiotic Strains The properties of the CNCM I-3689 strain were compared with those of various prior art strains, known for their probiotic properties.

The list of these strains is given in Table I below.

TABLE I

| Genus | Species | Name(s) | Publication number of patent applications |
|---|---|---|---|
| Lactobacillus | johnsonii | NCC533 = La1 = CNCM I-1225 | EP0577903 |
| Lactobacillus | acidophilus | NCFM | WO2004032639 |
| Lactobacillus | acidophilus | La-5 | |
| Lactobacillus | casei | Shirota | |
| Lactobacillus | paracasei | CRL431 = ATCC 55544 | |
| Lactobacillus | rhamnosus | LGG = ATCC 53103 | U.S. Pat. No. 4,839,281 |
| Lactobacillus | rhamnosus | HN001 = NM97/09514 | WO9910476 |
| Lactobacillus | plantarum | ATCC 14917 = DSMZ 20174 = WCFS1 | |
| Lactobacillus | plantarum | Probi 299v = DSM 9843 | WO9391823 |
| Lactobacillus | reuteri | DSMZ 20016 | |
| Lactobacillus | reuteri | Biogaia SD 2112 = ATCC 55730 | WO2004034808 |
| Bifidobacterium | breve | ATCC 15700 | |
| Bifidobacterium | breve | BBC50 = CNCM I-2219 | EP1189517 |
| Bifidobacterium | infantis | ATCC 15697 | |
| Bifidobacterium | longum | BB536 | |
| Bifidobacterium | longum | NCC2705 = CNCM I-2618 | |
| Bifidobacterium | animalis subsp. *lactis* | BB12 = ATCC 27536 | |
| Bifidobacterium | animalis subsp. *lactis* | HN019 = NM97/01925 | WO9910476 |

1—Antimicrobial Activity

The investigation of antimicrobial activities was carried out against three target pathogenic bacteria: *Escherichia coli* E1392-75-2A, *Salmonella enteritidis* NIZO B1241 and *Listeria monocytogenes* 4B. The lactic acid bacteria were cultured on Petri dishes in two different media: Elliker medium (Elliker et al., J. Dairy Sci., 39, 1611-1612, 1956), and TGE medium (tryptone-glucose-meat extract).

The dishes are incubated at 37° C. until bacteria colonies appear. The *Bifidobacterium* cultures were carried out under anaerobic conditions. A layer of agar containing BHI (brain-heart infusion) medium and the pathogen is then poured at the surface of the dishes. The dishes are incubated again at 37° C., for 24 h. The diameters of the areas of pathogen inhibition are then measured around each colony of lactic acid bacteria. Score 1 corresponds to a diameter of between 1 and 3 mm. Score 2 corresponds to a diameter of between 4 and 6 mm. Score 3 corresponds to a diameter of greater than 6 mm. Each experiment was carried out three times independently for each strain.

The scores obtained on the target pathogens in each experiment were added, so as to obtain, for each lactic acid bacterium, an overall score for antimicrobial activity.

The results are given in Table II hereinafter.

These results show that, among the strains tested, the CNCM I-3689 strain is, with the ATCC 55544 strain, the one which has the highest antimicrobial activity.

TABLE II

| Genus | Species | Reference | (1) E. coli/ Elliker | (2) Listeria/ Elliker | (3) Listeria/ TGE | (4) Salmonella/ Elliker | (5) Salmonella/ TGE | Anti-pathogen score (1 + 2 + 3 + 4 + 5) |
|---|---|---|---|---|---|---|---|---|
| Lactobacillus | paracasei subsp. paracasei | DN 114121 = CNCM I-3689 | 3 | 3 | 2 | 3 | 2 | 13 |
| Lactobacillus | paracasei | CRL431 = ATCC 55544 | 2 | 3 | 3 | 3 | 2 | 13 |
| Lactobacillus | rhamnosus | LGG = ATCC 53103 | 2 | 1 | 2 | 3 | 3 | 11 |
| Lactobacillus | plantarum | ATCC 14917 = DSMZ 20174 = WCFS1 | 2 | 1 | 2 | 3 | 2 | 10 |
| Lactobacillus | casei | Shirota | 2 | 3 | 1 | 1 | 2 | 9 |
| Lactobacillus | rhamnosus | HN001 = NM97/09514 | 1 | 1 | 2 | 3 | 2 | 9 |
| Lactobacillus | johnsonii | NCC533 = LA1 = I-1225 | 1 | 1 | 1 | 2 | 1 | 6 |
| Lactobacillus | plantarum | Probi 299v = DSM 9843 | 1 | 1 | 1 | 1 | 1 | 5 |
| Lactobacillus | acidophilus | La-5 | 1 | 1 | 2 | 0 | 1 | 5 |
| Lactobacillus | acidophilus | NCFM | 1 | 1 | 1 | 0 | 1 | 4 |
| Bifidobacterium | animalis subsp. lactis | BB12 = ATCC 27536 | 1 | 0 | 0 | 0 | 2 | 3 |
| Lactobacillus | reuteri | Biogaia SD 2112 ATCC 55730 | 0 | 1 | 0 | 1 | 0 | 2 |
| Bifidobacterium | longum | BB536 | 0 | 0 | 0 | 0 | 0 | 0 |
| Bifidobacterium | animalis subsp. lactis | HN019 = NM97/01925 | 0 | 0 | 0 | 0 | 0 | 0 |
| Lactobacillus | reuteri | DSMZ 20016 | 0 | 0 | 0 | 0 | 0 | 0 |
| Bifidobacterium | infantis | ATCC 15697 | 0 | 0 | 0 | 0 | 0 | 0 |
| Bifidobacterium | breve | BBC50 = I-2219 | 0 | 0 | 0 | 0 | 0 | 0 |
| Bifidobacterium | breve | ATCC 15700 | 0 | 0 | 0 | 0 | 0 | 0 |
| Bifidobacterium | longum | NCC2705 = CNCM I-2618 | 0 | 0 | 0 | 0 | 0 | 0 |

2—Immunomodulation

The immunomodulatory properties of the various lactic acid bacteria were evaluated by measuring the IL-10/IL-12 ratio.

Human blood samples, obtained from healthy individuals, were diluted to a 1:2 ratio with PBS-CA (Gibco) and purified using a Ficoll (Gibco) gradient. After centrifugation at 400×g for 30 min at 20° C., the PBMCs (peripheral blood mononuclear cells) were taken. Three washing steps were then carried out, and then the PBMCs were resuspended in an RPMI culture medium (Gibco) supplemented with 1% of fetal calf serum, 1% of L-glutamine (Gibco) and 150 µg/ml of gentamicin (Gibco). The PBMCs were counted under a microscope and adjusted to a concentration of $2\times10^6$ cells/ml, and then distributed, in aliquots of 1 ml, into 24-well cell culture plates (Corning, Inc.).

The Lactobacillus strains were cultured in MRS medium (de Man et al., J. Appl. Bacteriol. 23, 130-135, 1960), and the Bifidobacterium strains were cultured in MRS medium supplemented with 0.03% of L-cysteine (Sigma) under anaerobic conditions. All the strains were incubated at a temperature of 37° C. The growth of the bacteria was stopped in the stationary phase, and the bacteria were then washed and resuspended at a concentration of 3 MacFarlan units in PBS containing 20% glycerol.

A volume of 10 µl of bacterial preparation was added to each well of the plates containing the PBMCs (bacteria:cell ratio 10:1). The plates were incubated for 24 h at 37° C. under an atmosphere containing 5% $CO_2$. The supernatant was then drawn up, centrifuged at 2000 rpm and stored at −20° C.

The control bacterial strains, with known immunomodulatory properties, were included in the test. PBS-20% glycerol, without bacteria, was also used as a negative control. The experiment was carried out for each strain on PBMCs derived from three different donors.

The expression of the cytokines was measured by means of ELISA assays using commercial kits (Pharmingen, BD Biosciences). Two cytokines were studied: IL-10 and IL-12.

For each strain tested, the average of the IL-10/IL-12 ratio was calculated. These results are given in Table III below.

TABLE III

| Genus | Species | Reference | IL-10/IL-12 ratio |
|---|---|---|---|
| Lactobacillus | paracasei subsp. paracasei | DN 114121 = CNCM I-3689 | 11.8 |
| Lactobacillus | plantarum | Probi 299v = DSM 9843 | 12.7 |
| Lactobacillus | acidophilus | La-5 | 23.5 |
| Lactobacillus | acidophilus | NCFM | 23.6 |
| Lactobacillus | johnsonii | NCC533 = La1 = I-1225 | 23.7 |
| Lactobacillus | plantarum | ATCC 14917 = DSMZ 20174 = WCFS1 | 25.0 |
| Lactobacillus | reuteri | Biogaia SD 2112 ATCC 55730 | 25.4 |
| Bifidobacterium | longum | BB536 | 26.4 |
| Bifidobacterium | animalis subsp. lactis | HN019 = NM97/01925 | 28.7 |
| Bifidobacterium | animalis subsp. lactis | BB12 = ATCC 27536 | 32.4 |
| Lactobacillus | rhamnosus | LGG = ATCC 53013 | 34.5 |
| Lactobacillus | reuteri | DSMZ 20016 | 42.0 |
| Bifidobacterium | infantis | ATCC 15697 | 51.4 |
| Bifidobacterium | breve | BBC50 = I-2219 | 58.6 |
| Lactobacillus | casei | Shirota | 67.6 |
| Bifidobacterium | breve | ATCC 15700 | 68.5 |
| Bifidobacterium | longum | NCC2705 = CNCM I-2618 | 72.6 |
| Lactobacillus | rhamnosus | HN001 = NM97/09514 | 92.1 |
| Lactobacillus | paracasei | CRL431 = ATCC 55544 | 164.0 |

These results show that the CNCM I-3689 strain exhibits considerable anti-inflammatory properties on this model. None of the reference strains tested exhibits such good properties.

FIG. 1 represents the IL-10/IL-12 ratio of each bacterial strain as a function of its anti-pathogen score (arbitrary unit) determined above. This figure shows how much the CNCM I-3689 strain differs from the other strains tested.

3—Survival with Respect to Intestinal Stress

An in vitro model reflecting the conditions of intestinal stress was used.

Cultures of lactic acid bacteria are prepared in milk supplemented with yeast extract. The cultures are incubated for 24 to 48 h, depending on the species (until the stationary phase of the culture).

An artificial intestinal juice composed of porcine bile salts (at 3.3 g/l) and of $NaHCO_3$ carbonate buffer (at 16.5 g/l) is prepared. The pH is adjusted to 6.3. 1 ml of this intestinal juice is added to 100 µl of bacterial culture. The cultures are then incubated for 5 hours. Next, the bacterial populations before and after the stress are evaluated on dishes.

The values are expressed in the following way:

intestinal stress=log(cfu5 h/cfu0 h).

cfuXmin being the concentration of bacteria expressed as Colony Forming Units (CFUs) after X minutes of incubation.

For the intestinal stress, survival is good when the value is greater than −0.5, moderately good when the value is between −0.5 and −1.5, and poor when the value is less than −1.5.

The results are given in the following Table IV.

TABLE IV

| Genus | Species | Reference | Intestinal stress |
|---|---|---|---|
| Lactobacillus | paracasei subsp. paracasei | DN 114121 = CNCM I-3689 | −0.40 |
| Bifidobacterium | animalis subsp. lactis | HN019 = NM97/01925 | 3.40 |
| Bifidobacterium | infantis | ATCC 15697 | 2.79 |
| Lactobacillus | reuteri | Biogaia SD 2112 ATCC 55730 | 1.00 |
| Lactobacillus | johnsonii | NCC533 = La1 = I-1225 | 0.69 |
| Bifidobacterium | animalis subsp. lactis | BB12 = ATCC 27536 | 0.07 |
| Lactobacillus | paracasei | CRL431 = ATCC 55544 | 0.04 |
| Lactobacillus | rhamnosus | HN001 = NM97/09514 | 0.00 |
| Lactobacillus | rhamnosus | LGG = ATCC 53103 | −0.07 |
| Bifidobacterium | breve | ATCC 15700 | −0.14 |
| Bifidobacterium | longum | NCC2705 = CNCM I-2618 | −0.22 |
| Lactobacillus | acidophilus | La-5 | −0.23 |
| Lactobacillus | plantarum | ATCC 14917 = DSMZ 20174 = WCFS1 | −0.79 |
| Bifidobacterium | breve | BBC50 = I-2219 | −0.91 |
| Lactobacillus | plantarum | Probi 299v = DSM 9843 | −1.04 |
| Bifidobacterium | longum | BB536 | −1.12 |
| Lactobacillus | acidophilus | NCFM | −1.45 |
| Lactobacillus | casei | Shirota | −1.50 |
| Lactobacillus | reuteri | DSMZ 20016 | −1.91 |

4—Conclusion

The results illustrated in Tables II, III and IV above show that, among the various strains tested, the CNCM I-3689 strain is the only one to have both considerable antimicrobial properties and considerable anti-inflammatory properties, accompanied, in addition, by very good properties of resistance to intestinal stress.

EXAMPLE 2

Growth of the CNCM I-3689 Strain on Milk

The growth-on-milk properties of the CNCM I-3689 strain were tested using the following protocol:

A medium made up of skimmed milk reconstituted with water to which skimmed milk powder has been added was inoculated with the CNCM I-3689 strain ($5.6 \times 10^6$ cfu/g or $1.1 \times 10^7$ cfu/g).

The fermentative activity of this strain, which is linked to its growth, is measured by continuously monitoring the pH of the growth medium.

Figure 2:
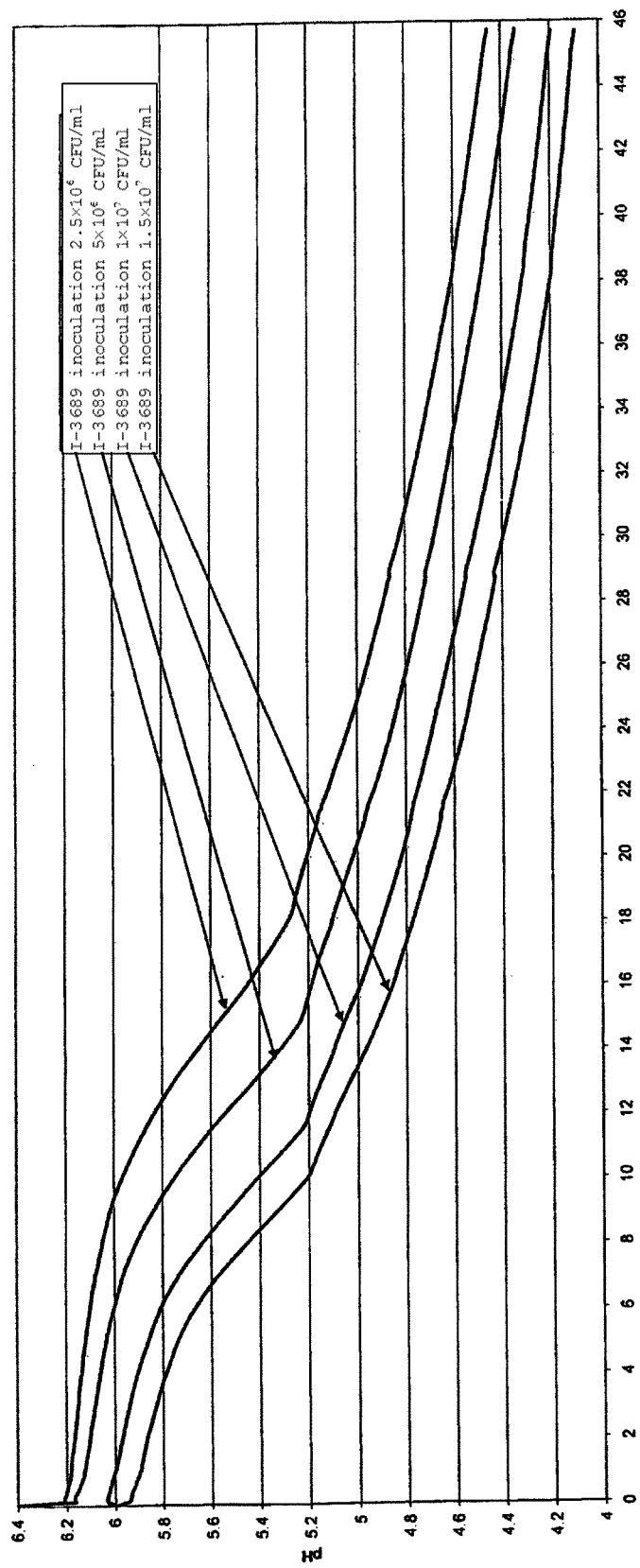
FIG. 2 represents the fermentative activity of the bacterial strain CNCM I-3689, which is measured by continuously monitoring the pH of the growth medium as a function of time and the proportion of inoculated bacterial strain ($5.6 \times 10^6$ cfu/g or $1.1 \times 10^7$ cfu/g).

The results are illustrated by the graph shown in FIG. 2.

These results show that the CNCM I-3689 strain is capable of growing efficiently on milk, and that it can therefore be used in the manufacture of fermented dairy products.

EXAMPLE 3

Molecular Typing of the CNCM I-3689 Strain

Many prokaryotic organisms have one or more CRISPR loci acronym for "*Clustered Regularly Interspaced Short Palindromic Repeats*" (Jansen et al., 2002, OMICS, Vol. 6, No. 1, 23-33). A CRISPR locus is characterized by non-contiguous repeat sequences (or DRs), generally of 21 to 37 base pairs (bp), separated by unique sequences, generally of 20 to 40 base pairs, called variable sequences ("spacers"). From one bacterial strain to the other, it is possible to observe differences regarding:

the number of CRISPR loci,
the position of the CRISPR loci in the genome,
the number of repeat sequences, and/or
the nature and/or the size of the variable sequences.

1—Identification of the CRISPR Locus of the CNCM I-3689 Strain

The CNCM I-3689 strain was sequenced. The analysis of its genome using the ERGO™ software series made it possible to identify a single CRISPR locus in this strain. This locus, which is 3323 bp in size, is located 20 base pairs downstream of the ORF RDBK00370. Its genomic DNA sequence is represented by the sequence SEQ ID NO: 1. It is composed of a repeat unit (GTTTTCCCCGCACAT-GCGGGGGTGATCC; SEQ ID NO: 2) which is identical to that of the CRISPR locus of the ATCC 334 strain (*Lactobacillus casei*), and of 54 variable sequences (spacers).

2—Construction of PCR Amplification Primers Specific for the CNCM I-3689 Strain

Several pairs of oligonucleotide primers were defined on the basis of the variable sequences of the CRISPR locus of the CNCM I-3689 strain. These primers were tested by PCR amplification on several bacterial strains in order to verify their specificity for the CNCM I-3689 strain.

One pair of primers was retained:
primer OFF2486 (CTCAACAGGATAAGTGCCAC; SEQ ID NO: 3), located in the $33^{rd}$ variable sequence of the CRISPR locus, at positions 2049-2068; TM=60° C.;
primer OFF2488 (GGTTGGCTGGGTTTAACGC; SEQ ID NO: 4), located in the $37^{th}$ variable sequence of the CRISPR locus, at positions 2093-2110; TM=60° C.

The PCR conditions retained are the following:
Reaction mixture:

| | |
|---|---|
| DNA: | 1 µl |
| dNTPs: | 4 µl |
| 10X buffer: | 5 µl |
| Primer OFF2486: | 0.3 µl |
| Primer OFF2488: | 0.3 µl |
| Ex taq ™ DNA polymerase: | 0.2 µl |
| Water: | 39.2 µl |

Cycles:

| | | |
|---|---|---|
| 95° C. | 5' | |
| 95° C. | 30" | |
| 61° C. | 30" | } × 30 |
| 72° C. | 45" | |
| 72° C. | 10' | |
| 10° C. | | |

The expected size of the PCR product from the CNCM I-3689 strain is 263 bp.

The pair of primers OFF2486/OFF2488 was tested on the CNCM I-3689 strain and on 18 other different strains of *Lactobacillus casei*, including the CNCM I-1518 and ATCC 334 strains. The CNCM I-1518 and ATCC 334 strains represent the negative controls since said primers cannot hybridize to the genomic DNA sequence of these strains under the PCR conditions described above.

Figure 3:
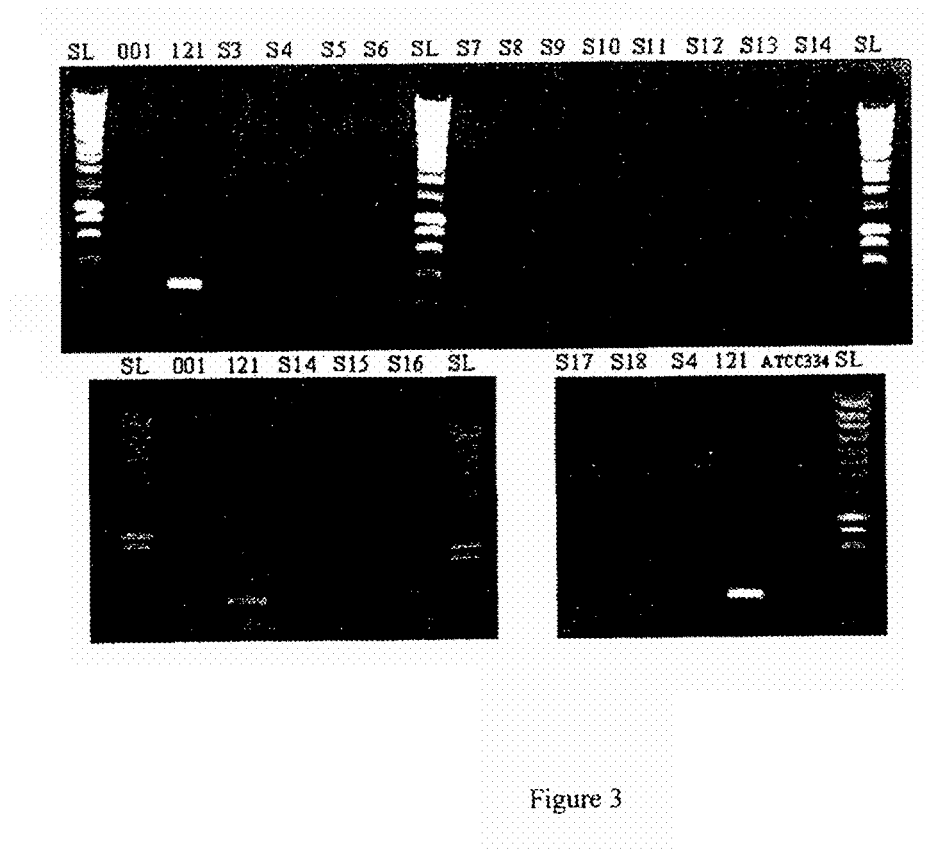
FIG. 3 represents an agarose gel electrophoresis of the PCR amplification products with a pair of primers specific to the CRISPR locus of the CNCM I-3689 strain, where "121" represents the CNCM I-3689 strain, "001" represents the CNCM-I-1518 strain, "S3" to "S18" represent, respectively, 16 different strains of *Lactobacillus casei*, and "SL" represents a molecular weight marker (SmartLadder; Eurogentec).

The results are illustrated by the agarose gel electrophoresis of the PCR amplification products, presented in FIG. 3, where "121" represents the CNCM I-3689 strain, "001" represents the CNCM I-1518 strain, "S3" to "S18" represent, respectively, 16 different strains of *Lactobacillus casei*, and "SL" represents a molecular weight marker (SmartLadder; Eurogentec).

These results show that the pair of primers OFF2486/OFF2488 is indeed specific for the CNCM I-3689 strain, since PCR amplification products of expected size (i.e. approximately 260 bp) were obtained only for this strain.

The invention claimed is:

1. An isolated *Lactobacillus paracasei* subsp. *paracasei* strain having antimicrobial and immunomodulatory properties, wherein the strain is deposited with the Collection Nationale de Cultures de Microorganismes under Accession number I-3689.

2. A composition comprising the isolated *Lactobacillus paracasei* subsp. *paracasei* strain as claimed in claim 1.

3. The composition as claimed in claim 2, wherein said composition is a food product.

* * * * *